(12) United States Patent
Bilton et al.

(10) Patent No.: US 9,155,838 B2
(45) Date of Patent: Oct. 13, 2015

(54) MEDICATED MODULE HAVING A DOUBLE NEEDLE GUARD

(75) Inventors: Simon Lewis Bilton, Leamington Spa (GB); Malcolm Stanley Boyd, Wellesbourne (GB); James Alexander Davies, Leamington Spa (GB); John David Cross, Northampton (GB); Aled Meredydd James, Dorridge (GB); David Moore, Elmesthorpe (GB); Daniel Thomas De Sausmarez Lintell, Rugby (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 344 days.

(21) Appl. No.: 13/520,692

(22) PCT Filed: Feb. 1, 2011

(86) PCT No.: PCT/EP2011/051408
§ 371 (c)(1),
(2), (4) Date: Feb. 26, 2013

(87) PCT Pub. No.: WO2011/095488
PCT Pub. Date: Aug. 11, 2011

(65) Prior Publication Data
US 2013/0197474 A1    Aug. 1, 2013

Related U.S. Application Data

(60) Provisional application No. 61/301,696, filed on Feb. 5, 2010.

(30) Foreign Application Priority Data

Apr. 23, 2010   (EP) .................................. 10160848

(51) Int. Cl.
*A61M 5/24*    (2006.01)
*A61M 5/315*   (2006.01)
(Continued)

(52) U.S. Cl.
CPC .............. *A61M 5/2448* (2013.01); *A61M 5/284* (2013.01); *A61M 5/31545* (2013.01);
(Continued)

(58) Field of Classification Search
CPC .......... A61M 5/24; A61M 2005/2403; A61M 2005/2407; A61M 5/2448; A61M 2005/2451; A61M 2005/247; A61M 2005/2474; A61M 2005/2485; A61M 2005/2488; A61M 2005/2492; A61M 5/2466; A61M 5/28; A61M 5/284; A61M 5/3202; A61M 5/3204; A61M 5/347; A61M 2005/3247; A61M 2005/32671; A61M 5/31528; A61M 5/326; A61M 5/3271; A61M 5/3294; A61M 5/3295
USPC ......... 604/82–83, 85–89, 173, 187, 191–193, 604/197, 506
See application file for complete search history.

(56) References Cited

U.S. PATENT DOCUMENTS
4,822,340 A    4/1989   Kamstra
(Continued)

FOREIGN PATENT DOCUMENTS
EP      0409180 A1     1/1991
(Continued)

OTHER PUBLICATIONS
EnglishTranslation of Notice of Reasons for Rejection for Japanese Patent Application No. 2012-551599 dated Nov. 11, 2014.
(Continued)

*Primary Examiner* — Quynh-Nhu H Vu
(74) *Attorney, Agent, or Firm* — McDonnell Boehnen Hulbert & Berghoff LLP

(57) ABSTRACT

A medicated module (100) is attachable to a drug delivery device (102). The medicated module (100) includes a housing (104) having a proximal end and a distal end, the proximal end has a connector (110) configured for attachment to a drug delivery device (102). The distal end contains a shuttle (112). A first needle (114) is fixed in the housing (104) and a second needle (116) is fixed in the shuttle (112). The medicated module (100) also includes a reservoir (118) in the housing (104) comprising a medicament (12). Further, the medicated module (100) includes a guard assembly (122) positioned in the housing (104) and configured to move in an axial direction during application to an injection site. Preferably, the medicated module (100) is locked out after at least two injections of the medicament (105) contained in the drug delivery device (102).

13 Claims, 10 Drawing Sheets

(51) Int. Cl.
    *A61M 5/32* (2006.01)
    *A61M 5/28* (2006.01)
    *A61M 5/31* (2006.01)
    *A61M 5/34* (2006.01)
    *A61M 5/178* (2006.01)

(52) U.S. Cl.
    CPC ............ *A61M 5/326* (2013.01); *A61M 5/3298* (2013.01); *A61M 5/2466* (2013.01); *A61M 5/288* (2013.01); *A61M 5/3146* (2013.01); *A61M 5/3155* (2013.01); *A61M 5/31525* (2013.01); *A61M 5/3271* (2013.01); *A61M 5/3294* (2013.01); *A61M 5/3297* (2013.01); *A61M 5/347* (2013.01); *A61M 2005/1787* (2013.01); *A61M 2005/3247* (2013.01); *A61M 2005/3267* (2013.01)

(56) References Cited

U.S. PATENT DOCUMENTS

| | | | | |
|---|---|---|---|---|
| 4,897,083 | A * | 1/1990 | Martell | 604/192 |
| 5,242,401 | A | 9/1993 | Colsky | |
| 6,562,002 | B1 * | 5/2003 | Taylor | 604/82 |
| 6,746,438 | B1 * | 6/2004 | Arnissolle | 604/411 |
| 6,884,237 | B2 * | 4/2005 | Asbaghi | 604/198 |
| 6,902,543 | B1 * | 6/2005 | Cherif-Cheikh et al. | 604/82 |
| 7,563,245 | B2 | 7/2009 | Mu | |
| 2001/0037087 | A1 * | 11/2001 | Knauer | 604/137 |
| 2003/0120209 | A1 | 6/2003 | Jensen et al. | |
| 2005/0075602 | A1 | 4/2005 | Cherif-Cheikh et al. | |
| 2006/0229562 | A1 * | 10/2006 | Marsh et al. | 604/164.01 |
| 2006/0276755 | A1 | 12/2006 | Sullivan et al. | |
| 2009/0018506 | A1 | 1/2009 | Daily et al. | |
| 2011/0137247 | A1 * | 6/2011 | Mesa et al. | 604/111 |

FOREIGN PATENT DOCUMENTS

| | | |
|---|---|---|
| EP | 0990446 A1 | 4/2000 |
| FR | 2799654 A1 | 4/2001 |
| JP | 4820290 | 7/1971 |
| JP | 4977487 | 11/1972 |
| JP | 2000102614 A | 4/2000 |
| JP | 2007511299 A | 5/2007 |
| WO | 0176665 A1 | 10/2001 |
| WO | 2007026163 A1 | 3/2007 |

OTHER PUBLICATIONS

Machine Translation of Description of WO 01/76665 A1.
International Preliminary Report on Patentability for Int. App. No. PCT/EP2011/051408, issued Aug. 7, 2012.

* cited by examiner

MEDICATED MODULE HAVING A DOUBLE NEEDLE GUARD

CROSS REFERENCE TO RELATED APPLICATIONS

The present application is a 35 U.S.C. 371 National Application of PCT/EP2011/051408 filed Feb. 1, 2011, which claims priority to U.S. Provisional Patent Application No. 61/301,696 filed Feb. 5, 2010 and European Patent Application No. 10160848.7 filed Apr. 23, 2010, the entire contents of which are incorporated entirely herein by reference.

FIELD OF THE PRESENT DISCLOSURE

Specific embodiments of this disclosure relate to medical devices and methods of delivering at least two drug agents from separate reservoirs using devices having only a single dose setter and a single dispense interface. A delivery procedure initiated by the user may cause a non-user settable dose of a second drug agent and a variable set dose of a first drug agent to be delivered to the patient. The drug agents may be available in two or more reservoirs, containers, or packages, each containing independent (single drug compound) or pre-mixed (co-formulated multiple drug compounds) drug agents.

BACKGROUND

Certain disease states require treatment using one or more different medicaments. Some drug compounds need to be delivered in a specific relationship with each other in order to deliver the optimum therapeutic dose. Here, combination therapy may be desirable, but not possible in a single formulation for reasons such as, but not limited to, stability, compromised therapeutic performance and toxicology.

For example, in some cases it might be beneficial to treat a person suffering from diabetes with a combination of a long acting insulin along with a glucagon-like peptide-1 (GLP-1). This GLP-1 is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

A number of potential problems can arise when delivering two active medicaments or "agents" simultaneously. As just one example, the two active agents may interact with each other during the long-term, shelf life storage of the formulation. Therefore, there are certain advantages to storing the active components separately and combine them at the point of delivery, e.g. injection, needle-less injection, pumps, or inhalation. However, the process for combining the two agents needs to be simple and convenient for the user to perform reliably, repeatedly and safely.

One further concern is that the quantities and/or proportions of each active agent making up the potential combination dose or therapy may need to be varied for each user or at different stages of their therapy. Again, as just one example, one or more active agents may require a titration period to gradually introduce a patient to a "maintenance" dose. A further example would be if one active agent requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional concerns arise where a multi-drug compound therapy is required, because certain users cannot cope with having to use more than one drug delivery system or make the necessary accurate calculation of the required dose combination. This is especially true for users with dexterity or computational difficulties.

Other problems could arise where a user may attempt to re-use a non-sterile needle after a certain dose combination has been delivered. Using such a non-sterile needle may lead to the transmission of certain diseases (septicaemia) and therefore there exists a need for a medicated module that prevents needle re-use. There is a further concern of inadvertent needle sticks with certain needle assemblies where the injection needle is not concealed or covered, especially after use when a needle may be contaminated with blood. As such, there is also a general need to reduce certain patient's needle anxiety that may heighten a patient's fear or phobia of exposed needles.

Accordingly, there exists a strong need to provide devices and methods for the delivery of two or more medicaments in a single injection or delivery step that is simple and safe for the user to perform and that also tends to reduce a patient's anxiety towards injections or needles.

Problem to be Solved

The problem to be solved by the present invention is to provide a medicated module, a drug delivery system and a method of dispensing a medicament where the administration of a medicament is improved.

SUMMARY

In one aspect, a medicated module attachable to a drug delivery device is disclosed. The medicated module comprises a reservoir for retaining a medicament. In a preferred embodiment, the drug delivery device comprises a primary reservoir of a first medicament. The medicated module may comprise a secondary reservoir comprising a second medicament. The medicated module, in particular the secondary reservoir, may be pre-filled with the second medicament when the medicated module is attached to the device, in particular before fluid communication is established between the secondary reservoir and at least one of the first and the second needle cannula. The drug delivery device, in particular the primary reservoir, is preferably filled with first medicament before the module is attached to the device. The drug delivery device may be an injection device, and, in particular, a pen-type injection device. The device may be suitable to set and dispense a dose of the first medicament before the medicated module is attached to the device or after the medicated module was removed from the device. Accordingly, the device may be suitable to form a stand-alone device, configured to operate also in absence of the medicated module, for example. For this purpose, a needle cannula may be, preferably removably, attachable to the distal end of the device.

The medicated module may comprise a housing having a proximal end and a distal end. The proximal end may have a connector configured for attachment to a drug delivery device. The reservoir may be positioned within the housing by a first biasing member and a second biasing member. The first biasing member may comprise a first wavy spring and the second biasing member may comprise a second wavy spring. Furthermore, the medicated module may contain a shuttle configured for axial movement relative to the housing. The shuttle may be located at the distal end of the housing. The medicated module may be a medicated needle or medicated needle assembly as described later on. The medicated module may comprise a first needle cannula. The medicated module may comprise a second needle cannula. The reservoir of the module may be arranged in the axial direction between the first and the second needle cannula. The needle cannulae may be adapted and arranged for establishing fluid communication with the reservoir of the module. The distal end of the second needle cannula may be configured for being applied to an injection site. The proximal end of the second needle cannula may be configured for piercing the reservoir of the module, in particular a seal or septum arranged at the distal end of the secondary reservoir. The distal end of the first needle cannula may be configured for piercing the reservoir of the module, in particular a seal or septum arranged at the proximal end of the secondary reservoir. The proximal end of the first needle cannula may be configured for piercing the primary reservoir, in particular a seal or septum arranged at the distal end of the primary reservoir. The first needle may be permanently or releasably fixed in the housing. The first needle may be fixed in the housing before the module is attached to the device. The second needle may be permanently or releasably fixed in the shuttle. In particular, the second needle may be fixed in the shuttle before the module is attached to the device. In one embodiment, the shuttle is configured for axial movement so as to cause the first and second biasing members to compress and thereby allow fluid communication between the medicament and the first and second needles. In particular, the shuttle is configured for movement in the proximal direction with respect to the housing. The shuttle may be adapted and arranged to be moved in the direction of the primary reservoir of the device for establishing fluid communication. The shuttle may be, at least partly, moved with respect to the reservoir of the module. The medicated module may comprise a trigger member. The trigger member may be moveable, in particular axially moveable, with respect to the housing. The trigger member may be configured to mechanically cooperate with the shuttle for moving the shuttle with respect to the housing. Movement of the shuttle may establish the fluid communication between the medicament and the first and second needles.

The medicated module may comprise a bypass. The bypass may be configured for bypassing the reservoir of the medicated module. At specific states of the medicated module, in particular when the medicated module is attached to the device, the first and second needles may be in fluid communication with the bypass. In particular, the needles may be in fluid communication with the bypass before a first application to an injection site, whereby a priming operation is enabled.

The medicated module may comprise at least one needle guard. The respective needle guard is preferably adapted and arranged to provide protection against at least one of the first and the second needle and configured to move in an axial direction when the needle guard is applied to an injection site. In particular, the needle guard may prevent accidental needle sticks. The needle guard may comprise a biasing member, such as a spring. Preferably, when the needle guard is retracted in a proximal direction, the biasing member may exert a force on the needle guard towards a distal direction. Thereby, after a retraction of the needle guard, the needle guard may return in an extended position. In one embodiment, the needle guard may be lockable such that in a locked state axial movement of the needle guard is prevented. As an example, the needle guard may be locked in a state where it is extended in the distal direction and covers the second needle. Thus, a further injection procedure may be prevented.

Accordingly, the needle guard may lock out the second needle after the second needle has been used to inject more than one dose of the medicament contained in the primary reservoir such that the second needle is disabled from being used for a further injection. The needle guard may be configured to move in an axial direction, e.g. a proximal direction of the medicated module when applied to an injection site.

The medicated module may comprise a needle guard assembly. The guard assembly may comprise several parts, for example a first and a second needle guard. The trigger member may comprise at least one of the needle guards. The needle guards may be operably connected to move together axially towards the proximal end of the housing during a first injection, and in particular, during a first application to an injection site. The medicated module, and, in particular, the distal end of the housing may be configured such that the shuttle is locked from axial movement when a needle guard, and, in particular, the first needle guard is moved axially towards the proximal end of the housing. Thereby, a permanent fluid communication between the needles and the reservoir may be achieved. The first needle guard may be locked during axial movement of the first needle guard in proximal direction such that a relative axial movement of the housing and the first needle guard is disabled. In particular, the proximal end of the housing may have a lock to engage the needle guard. The second needle guard may be movable in a distal direction after axial movement in the proximal direction during a first application to an injection site. The biasing member may be operably connected to the second needle guard. Thereby, the second needle guard may be urged back into an extended position, when the first needle guard is locked in a retracted position. The second needle guard may be locked to the first guard when the second guard is in a second extended position. The second extended position may be reached by the second needle guard after a second injection. By locking the second needle guard to the first needle guard, a relative axial movement of the second guard and the first guard is disabled. Thereby, a further injection may be prevented. The medicated module, and, in particular, the second guard may have indicia visible to a user when the second guard is locked to the first guard.

According to a first specific embodiment, a medicated module attachable to a drug delivery device is provided, wherein the drug delivery device comprises a primary reservoir of a first medicament and wherein the medicated module comprises a second medicament. The medicated module comprises a reservoir comprising the second medicament and a housing having a proximal end and a distal end. The housing is configured for attachment to the drug delivery device. The medicated module further comprises a first needle fixed in the housing and a second needle fixed in a shuttle. The shuttle is configured for axial movement relative to the housing, wherein a movement of the shuttle in axial direction opens fluid communication between the secondary reservoir and at least one of the first and the second needle.

According to a further specific embodiment, a medicated module attachable to a drug delivery device is provided. The medicated module comprises a housing having a proximal end and a distal end, where the proximal end has a connector configured for attachment to a drug delivery device. The distal end contains a shuttle. The medicated module further comprises a first needle fixed in the housing, a second needle fixed in the shuttle and a reservoir in the housing comprising a medicament. Moreover, the medicated module comprises a guard assembly positioned in the housing and configured to move in an axial direction during application to an injection site. The guard assembly comprises a first guard and a second guard.

In a preferred embodiment a master drug compound, such as insulin, contained within a multiple dose, user-selectable device could be used with a single use, user-replaceable, module that contains a single dose of a secondary medicament and the single dispense interface. When connected to the primary device, i.e., the drug delivery device, the secondary compound is activated/delivered on dispense of the primary compound. Although our disclosure specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used.

In the following, the term "insulin" shall mean insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala (B26) human insulin; Des(B28-B30) human insulin; Des (B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH$_2$).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

In a further aspect, the present disclosure relates to a needle assembly for use with a drug delivery device. The needle assembly may include a housing configured for attachment to a drug delivery device. The needle assembly may comprise a medicament contained within the drug delivery device. The needle assembly may further include an injection needle. The injection needle may be configured such that it is in fluid communication with the medicament contained within the drug delivery device. The injection needle may be located in a housing of the needle assembly. Further, the needle assembly may include a needle guard or a needle guard assembly as described above. The needle guard or needle guard assembly may be configured such that it locks out the injection needle in a defined state of the drug delivery device. Preferably, when the injection needle is locked out, a further use of the injection needle is prevented. In one embodiment, the needle guard is locked after the injection needle has been used to inject more than one dose of the medicament contained within the drug delivery device. In particular, the needle guard may lock out the injection needle after the injection needle has been used to inject two doses of the medicament contained within the drug delivery device. The needle assembly may comprise a dose of a medicament. The needle assembly may comprise a medicated module.

According to a specific embodiment, a needle assembly is provided, the needle assembly comprising a housing configured for attachment to a drug delivery device and a medicament contained within the drug delivery device. The needle assembly further comprises an injection needle configured within the housing such that the injection needle is in fluid communication with the medicament contained within the drug delivery device. The needle assembly comprises a needle guard that locks out the injection needle after the injection needle has been used to inject more than one dose of the medicament contained within the drug delivery device.

In yet a further aspect, a drug delivery system is disclosed. The drug delivery system may be configured to deliver two or more medicaments. In one embodiment, the drug delivery system is operable through a single dose setter and a single dispense interface. The drug delivery system may include a housing, which may contain a dose setter, in particular a single dose setter. The dose setter may be operably connected to a primary reservoir of medicament containing at least one drug agent. Furthermore, the drug delivery system may comprise a dose button, which may be operably connected to the primary reservoir of medicament. The drug delivery system may further include a medicated module, and, in particular, the medicated module as described above. The medicated module may be configured for fluid communication with the primary reservoir. The medicated module may comprise a proximal end and a distal end, where the proximal end may have a connector configured for attachment to the housing. The medicated module may further include a secondary reservoir containing a second medicament. The secondary reservoir may be sealed. The medicated module may comprise an output needle. Still further, the medicated module may include a needle guard or a needle guard assembly as described above. The needle guard or needle guard assembly may be configured such that the needle guard or at least one of the needle guards are locked after axial displacement. In particular, the needle guard assembly may comprise a first and a second guard and may be configured such that the first guard is locked after axial displacement. In accordance with this embodiment, a single activation of the dose button may cause medicament from the primary reservoir and the second medicament from the secondary reservoir to be expelled through the output needle when the first guard moves axially.

According to a first specific embodiment, a drug delivery system to deliver two or more medicaments comprising a medicated module as described above is provided. The drug delivery system further comprises a primary reservoir of medicament containing at least one drug agent, where the medicated module is configured for fluid communication with the primary reservoir.

According to a further specific embodiment, a drug delivery system to deliver two or more medicaments is provided. The drug delivery system is operable through a single dose setter and a single dispense interface and comprises a housing containing a single dose setter operably connected to a primary reservoir of medicament containing at least one drug agent. The device further comprises a dose button operably connected to the primary reservoir of medicament. The device comprises a medicated module configured for fluid communication with the primary reservoir, where the medicated module comprises a proximal end and a distal end, where the proximal end has a connector configured for attachment to the housing. The medicated module further comprises a sealed secondary reservoir containing a single dose of a second medicament and an output needle. Moreover, the medicated module comprises first and second guards, where the first guard is locked after axial displacement and wherein a single activation of the dose button causes medicament from the primary reservoir and the second medicament from the secondary reservoir to be expelled through the output needle when the first guard moves axially.

A further aspect relates to a method of dispensing a non-user settable dose of one medicament and a variable dose of a primary medicament from separate reservoirs. The method is used for testing purposes and does not comprise a treatment of the human or animal body by surgery or therapy. The method comprises, in combination, the steps of
   Attaching a medicated module as previously described to a drug delivery device;
   Setting a dose of a first medicament contained in a primary reservoir of the drug delivery device using a single dose setter of the drug delivery device;
   Priming the drug delivery device using the first medicament;
   Applying at least one of the needle guards to skin to insert the output needle causing the first guard to move axially and lock in a retracted position;
   Activating a dose button on the drug delivery device to cause the set dose of the first medicament from the primary reservoir to flow in a distal direction; and
   Forcing the set dose of the first medicament and the single dose of the second medicament through an output needle.
The method further comprises the steps of
   Injecting a second dose of the first medicament and
   Locking out the second needle guard after the second dose of the medicament is injected such
that the second needle guard is disabled from moving axially.

In still yet another embodiment, a method of utilizing a needle assembly to inject at least two doses of medicament from a reservoir is provided. The needle assembly may be designed and configured as described above. The method includes (i) injecting a first dose of the medicament from a reservoir, (ii) injecting a second dose of the medicament from the reservoir, and (iii) locking out the needle assembly after the second dose of the medicament is injected. Preferably, by locking out the needle assembly, a further use of the injection needle is prevented. As an example, the needle guards or at least one of the needle guards may be locked in a state where it is extended in the distal direction and fully covers the injection needle. The method may further comprise the steps of performing a priming step before the step of injecting the first dose of the medicament from the reservoir or after the step of injecting the first dose of the medicament from the reservoir.

In still yet another embodiment, a method of dispensing a non-user settable dose of one medicament and a variable dose of a primary medicament from separate reservoirs is provided. The method includes attaching a medicated module to a drug delivery device. The medicated module may be designed and configured as described above. In a specific embodiment, the medicated module comprises a proximal end and a distal end, where the proximal end has a connector configured for attachment to the housing. Furthermore, the medicated module includes a sealed secondary reservoir containing a second medicament, and an output needle. The medicated module includes a needle guard assembly as described above. In a specific embodiment, the needle guard comprises first and second guards. The first guard is locked after axial displacement. The method also includes setting a dose of a first medicament contained in a primary reservoir using a single dose setter of the drug delivery device. The method further includes priming the output module using the first medicament and applying at least one of the guards to the skin to insert the output needle. Thereby, the first guard is caused to move axially and lock in a retracted position. The method further includes activating a dose button on the drug delivery device to cause the set dose of the first medicament from the primary reservoir to flow in a distal direction. Furthermore, the method includes forcing the set dose of the first medicament and a dose of the second medicament through the output needle.

The method may further comprise the steps of injecting a second dose of the first medicament and locking out the second guard after the second dose of the medicament is injected. Thereby, the second guard is disabled from moving axially.

In specific embodiments, the methods described above are used for testing purposes such that they do not comprise a treatment of the human or animal body by surgery or therapy.

A further aspect relates to a method for testing a medicated module. The method is not intended for testing purposes in connection with the human or animal body. The method may be used for testing the functionality of the module. The method may comprise the steps of:
   A) Providing the previously described medicated module.
   B) Attaching the medicated module to a drug delivery device. The device may comprise a primary reservoir of medicament containing at least one drug agent. Preferably, the device comprises a plurality of variable doses of the medicament.
   C) Setting a dose of the medicament using a single dose setter of the drug delivery device;
   D) Performing a priming step by means of activation of a dose button on the drug delivery device such that medicament of the primary reservoir is expelled through the second needle. In particular, the medicament of the primary reservoir may bypass the second medicament held in the reservoir of the module.
   E) Moving the first and second needle guards proximally such that the shuttle is moved proximally and such that fluid communication is established between the needles and the reservoir.
   F) Setting a variable dose of the medicament of the primary reservoir.
   G) Activating the dose button on the drug delivery device to cause the set dose of the first medicament from the primary reservoir to flow in a distal direction.
   H) Forcing the set dose of the first medicament and the single dose of the second medicament through the second needle.

Furthermore, the method may comprise the step of

I) Locking the first needle guard in a retracted position after the first needle guard was moved proximally and after fluid communication was established.

Furthermore, the method may comprise the steps of

J) Moving the second needle guard proximally.

K) Setting a further variable dose of the medicament of the primary reservoir.

L) Activating the dose button on the drug delivery device to cause the further dose of the first medicament from the primary reservoir to flow in the distal direction.

M) Forcing the further dose of the first medicament through the second needle.

N) Locking the second needle guard in an extended position after the further dose of the medicament was expelled.

These as well as other advantages of various aspects of the present invention will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which.

DETAILED DESCRIPTION

Specific embodiments of the disclosed medicated module and drug delivery system enable administering a fixed predetermined dose of a second medicament (secondary drug compound) and a potentially variable dose of a first medicament (primary drug compound) through a single output or drug dispense interface such as a double ended needle. Setting the dose of the primary medicament by the user may automatically determine the fixed dose of the second medicament. This fixed dose of the second medicament may be a single dose. Furthermore, a second dose of a potentially variable dose of the first medicament may be administered through the same single dispense interface. The term drug dispense interface may be, in the context of this disclosure, any type of outlet that allows the two or more medicaments to exit the drug delivery system and be delivered to the patient. In a preferred embodiment the single drug dispense interface comprises a hollow needle cannula.

In a preferred arrangement, the drug dispense interface comprises a needle cannula (hollow needle) and a needle guard assembly that includes both a first and second needle guard. The needle guard assembly is designed so as to lock out the injection needle after the injection needle has been used to inject more than one dose of the medicament contained within the drug delivery device, e.g., allow a user to administer (i) a first dose that includes the fixed predetermined dose (i.e., non-user-settable dose) of the second medicament and a potentially variable dose of a first medicament and (ii) a second dose that includes a potentially variable dose of a first medicament. In the preferred arrangement, the needle guard assembly locks out in a distal position after a user administers the second dose of the first medicament. In one preferred arrangement, the user may prime the device prior and/or after the first administered dose.

Administering the second dose may be useful or beneficial for a plurality of reasons. For example, this second dose may be useful for topping up the first dose with additional medicament. As another example, the second dose may also be useful for splitting doses as required by a user. A user may be called upon to split a dose due to patient discomfort experienced part way through an injection (e.g., due to injecting into scar tissue). A patient may also be called upon to split doses so as to enable a dose to be split across two drug delivery devices, i.e., to exhaust all the medicament from a first device (e.g., a pen type injection device) and then take the remainder of the dose from a second device (e.g., a second pen). Other reasons are possible as well.

Figure 1:
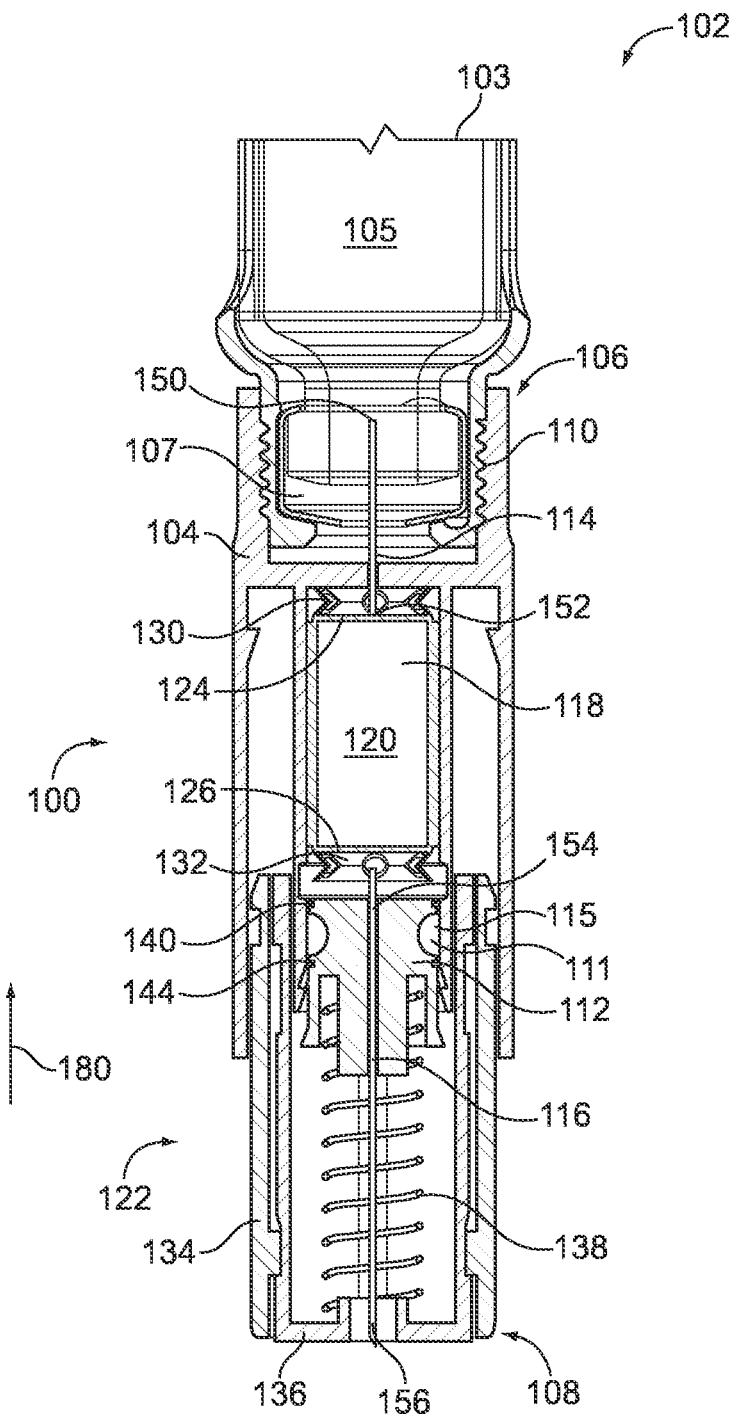
FIG. 1 illustrates a sectional view of one arrangement of a medicated module attached to a drug delivery device.
Figure 7:
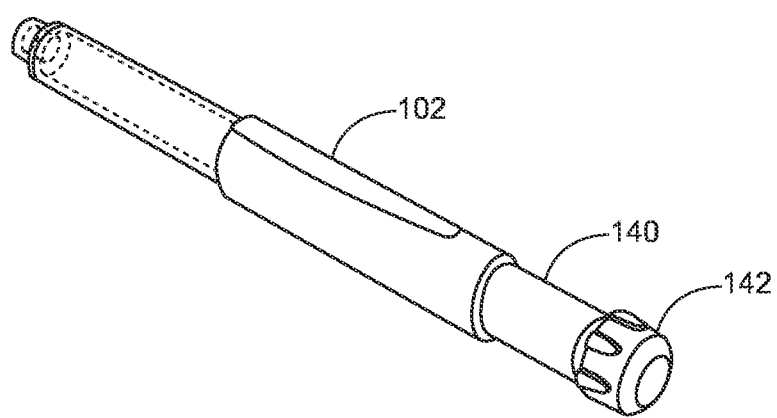
FIG. 7 illustrates one possible drug delivery device that can be used with the medicated module illustrated in FIG. 1.

FIG. 1 illustrates a preferred arrangement of a medicated module 100 attached to a drug delivery device 102. Only a portion of drug delivery device 102 is illustrated in FIG. 1. As explained below, such a drug delivery device could comprise a pen type injection device, as illustrated in FIG. 7.

Drug delivery device 102 contains a device cartridge 103 that includes a primary first medicament 105, such as insulin. Medicated module 100 includes a housing 104 that has a proximal end 106 and a distal end 108. The proximal end has a connector 110 that is configured for being releasably attached to drug delivery device 102.

Figure 2:
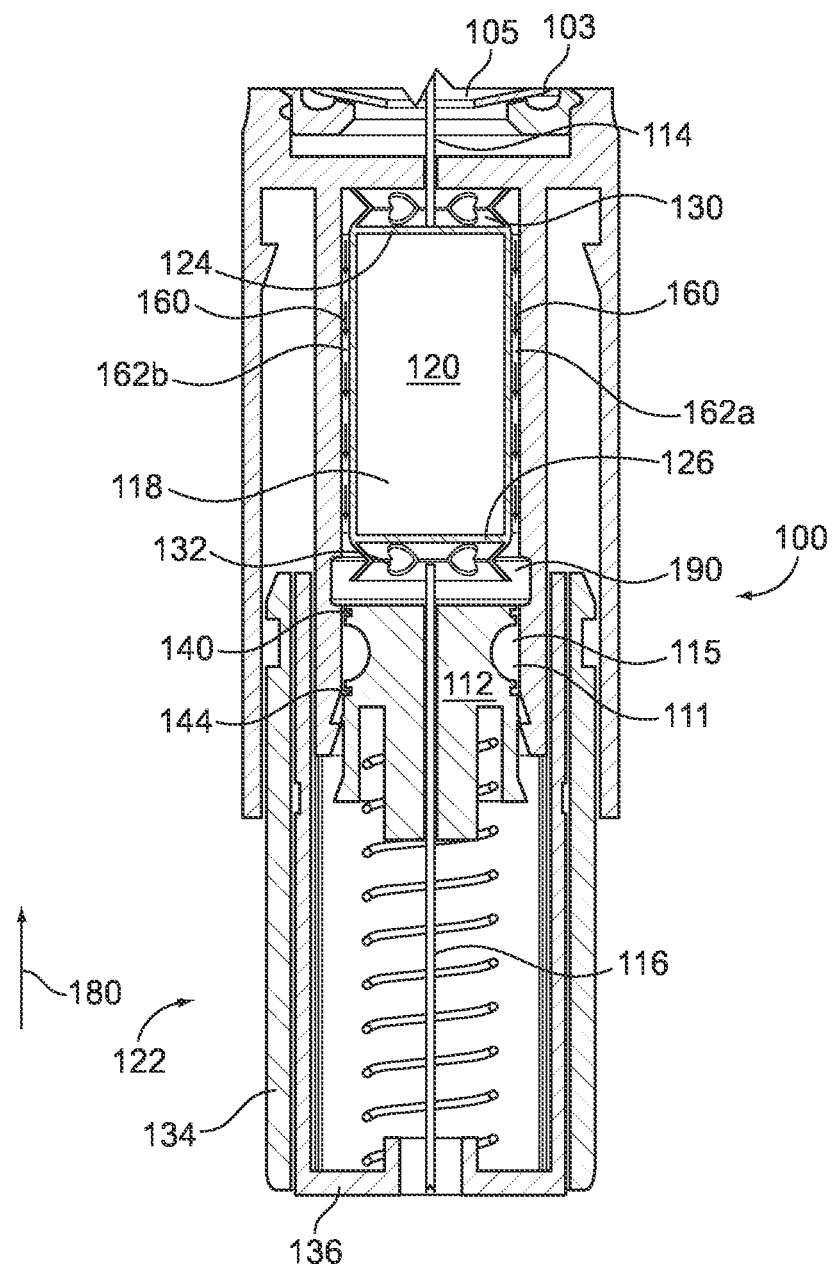
FIG. 2 illustrates a close-up sectional view of the medicated module of FIG. 1.
Figure 3:
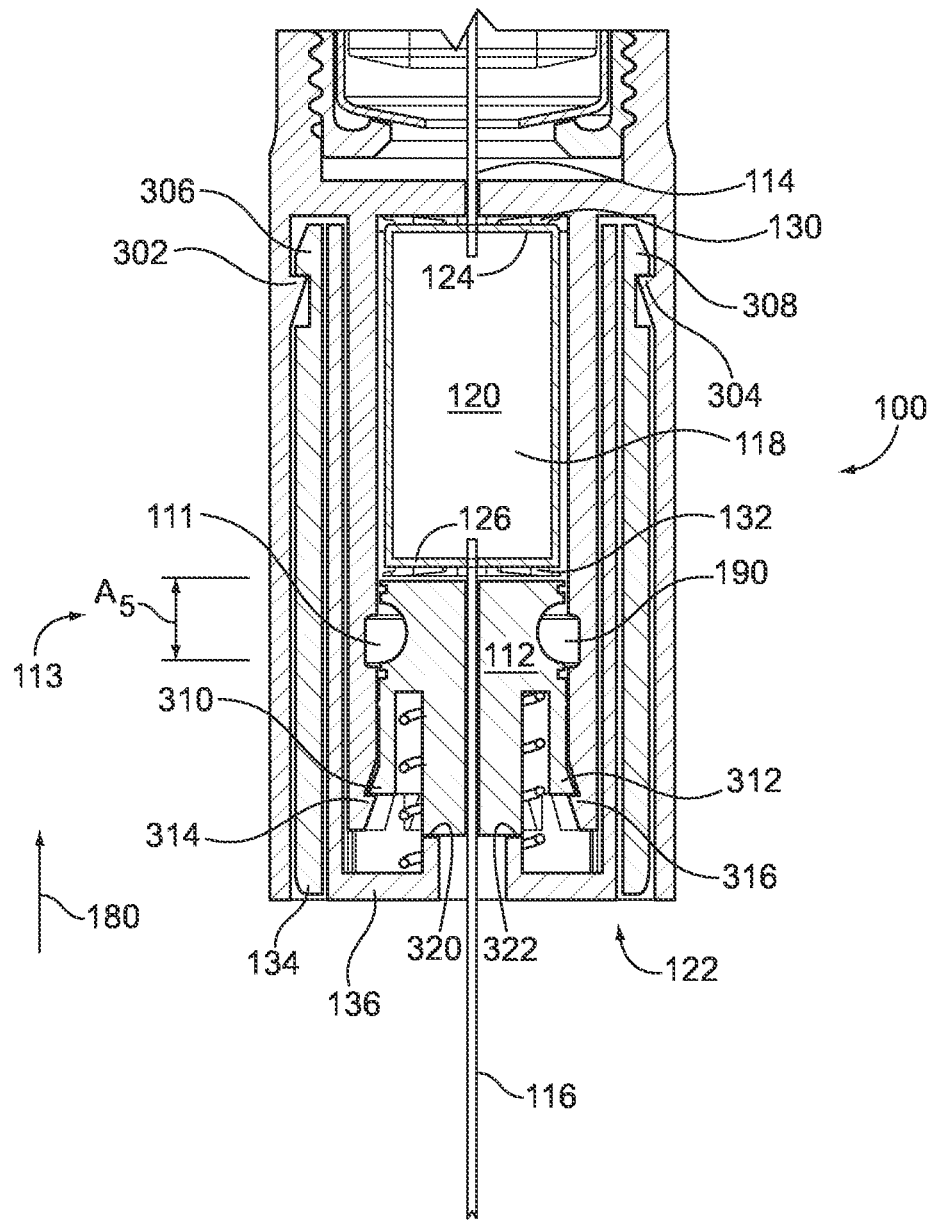
FIG. 3 illustrates a sectional view of the medicated module of FIG. 1 in a first retracted position.

The distal end 108 includes a shuttle 112. As will be explained in greater detail below, this shuttle 112 moves in a proximal direction when the medicated module 100 is used to administer a first injection. Preferably, the shuttle 112 comprises a toroidal cutout 111 near a proximal end 115 of the shuttle 112. The shuttle 112 is maintained within a cavity defined by the housing 104 by way of a first sealing ring 140 and a second sealing ring 144. These sealing rings 140, 144 provide a fluid seal between the shuttle 112 and a bypass cavity 190 as the shuttle 112 moves from a first distal position (FIGS. 1 and 2) to a second proximal position (FIG. 3).

The medicated module 100 has a first needle 114 that is fixed in housing 104. The module 100 has a second needle 116 that is fixed in shuttle 112. The housing 104 also contains a reservoir 118 located between the first and second needles 114, 116, and this reservoir contains a second medicament 120. In one preferred arrangement, this reservoir contains a single dose of the second medicament 120. The reservoir 118 is axially arranged between the needles 114, 116. The needles 114, 116 are positioned to establish fluid communication with the reservoir 118. A guard assembly 122 is positioned in housing 104 and this guard assembly 122 is configured to move in an axial direction 180 (defined by arrow 180) during application to an injection site, such as an injection site of a human user.

As mentioned, the housing 104 contains a reservoir 118 that contains a second medicament 120. This reservoir is biased within the housing between a first and a second biasing member such as a proximal wavy spring 130 and a distal wavy spring 132. These biasing members 130, 132 compress under an axially directed force created in part by the shuttle 112 and the inner needle guard 136. As illustrated in FIGS. 1 and 2, these biasing members are in an uncompressed or relaxed state.

Most preferably, this second medicament 120 comprises a single dose of a medicament, such as a single dose of GLP-1 or alternatively a pre-mix of medicaments. In one preferred arrangement, the reservoir 118 comprises a capsule comprising a first and a second end that is sealed with first (or top) and second (or bottom) pierceable membranes 124, 126. Such a construction provides a hermetically sealed reservoir for the second medicament 120.

When the medicated module 100 is first connected to the drug delivery device 102, the first needle 144 pierces a septum 107 of a device cartridge 103 in the drug delivery device 102. As discussed above, the device cartridge may contain a primary medicament 105, in particular the cartridge 103 is filled at least party with the primary medicament 105 before the module 100 is attached to the device 102. Most preferably, the primary medicament 105 is a type of insulin. The second needle 116 may be used to first subcutaneously inject the primary medicament 105 contained in the cartridge 103 along with medicament 120 contained in the reservoir 118 of medicated module 100.

As mentioned, the reservoir 118 located between the two needles 114, 116 preferably comprises the top seal 124 and the bottom seal 126. The top or proximal seal 124 resides adjacent the proximal wavy spring 130 and the bottom or distal seal 126 resides directly adjacent the distal wavy spring 132. Before injection, neither the first needle nor the second needle pierce the seals since the wavy springs 130, 132 bias the reservoir 118 away from the piercing ends of the first and second needles, 114 and 116 respectively.

The first needle 114 is rigidly affixed in an upper surface of the housing 104. Preferably, this first needle 114 comprises a double ended needle having a first piercing end 150 (i.e., a proximal end) and a second piercing end 152 (i.e., a distal end). In this preferred arrangement, when the medicated module 100 is initially mounted to the drug delivery device 102 as illustrated in FIG. 1, the first piercing end 150 pierces a membrane 107 of the cartridge 103 but the second piercing end 152 does not yet pierce the first or top seal 124 of the reservoir 118. As such, the first medicament 105 of the cartridge 103 is not in fluid communication with the second medicament 120 contained in the reservoir 118.

The second needle 116 is rigidly affixed in a lower surface of the housing 104, such as in shuttle 112. Preferably, this second needle 116 comprises a double ended needle having a first piercing end 154 and a second piercing end 156. In this preferred arrangement, when the medicated module 100 is initially mounted to the drug delivery device 102 as illustrated in FIG. 1, the first piercing end 154 does not pierce the bottom seal 126 of the reservoir 118. In addition, in this preferred arrangement, the second piercing end 156 of the second needle 116 is illustrated as being substantially concealed from a user's view by way of the needle guard assembly 122. This concealment may help reduce any needle anxiety that a patient may be experiencing.

In one arrangement, the medicated module 100 is preferably self-contained and may be provided as a sealed and sterile disposable module. Such a module comprises an attachment means, such as connector 110, compatible to the attachment means at the distal end of the drug delivery device 102. Although not shown, the medicated module 100 could be supplied by a manufacturer contained in a protective and sterile capsule or container where the user would peel or rip open a seal or the container itself to gain access to the sterile medicated module 100. In some instances it might be desirable to provide two or more seals for each end of the medicated module 100.

One example of a drug delivery device 102 that may be used with the medicated module 100 is illustrated in FIG. 7. Any known attachment means can be used, including permanent and removable connection means. Threads, snap locks, snap fits, luer locks, bayonet, snap rings, keyed slots, and combinations of such connections can be used to attach medicated module 100 to drug delivery device 102. As just one example, FIG. 1 illustrates the connector 110 comprising screw threads.

The arrangement shown in FIG. 1 has the benefit of the second medicament 120 as being contained entirely within the medicated module 100. This can minimize the risk of material incompatibility between the second medicament and the materials used in the construction of the medicated module 100.

Returning to FIG. 1, the guard assembly 122 includes a first guard 134 and a second guard 136. The first guard 134 may be hereinafter referred to as an "outer guard" and the second guard 136 may be hereinafter referred to as an "inner guard." The outer and inner guards 134, 136 are preferably operably connected such that the guards 134, 136 initially move together toward the proximal end 106 of the medicated module 100. Further, the guard assembly 122 may comprise a biasing member 138. The biasing member 138 is preferably a compression spring that is operably connected to the inner guard 136.

Preferably, the needle guard assembly 122 is tubular-shaped and in a relaxed position, as illustrated in FIG. 1, substantially conceals the second needle 116. While substantially concealing the second needle, the needle guard also helps to prevent inadvertent needle sticks. During a first injection step where a user initiates the injection, the needle guard assembly 122 is free to be moved in a proximal direction towards the drug delivery device (illustrated by arrow 180 in FIGS. 1-3).

The medicated module 100 and outer and inner needle guards 134, 136 are designed in order to allow (i) a first dose that includes the fixed predetermined dose of the second medicament and a potentially variable dose of a first medicament and (ii) a second dose that includes a potentially variable dose of a first medicament. Further, the medicated module 100 and outer and inner needle guards 134, 136 are also designed so as to lock-out the medicated module after the second dose. Still further, the medicated module 100 and the outer and inner needle guards 134, 136 are designed in order to allow priming of the drug delivery device as needed without loss of the second medicament 120. The mechanical action of the needle guard assembly 122 is described in more detail below.

In one preferred arrangement, both the inner and outer guards 134, 136 comprise a colored material. For example, the outer guard 134 may comprise a first color and the inner guard 136 may comprise a second color that is different than the first color. As just one example, the outer guard 134 may comprise a yellow color and the inner guard 136 may comprise a blue color. Therefore, in an initial unused state of the medicated module 100 as illustrated in the FIG. 1, when both the inner and outer needle guards 136, 134 reside in a distal or unlocked state, the user of the module would recognize the state of the unlocked module since both needle guards would combine to appear green in color (yellow combined with blue). As will be explained below, after a first injection when the outer "yellow" needle guard 134 is locked out in a proximal position, the user would be able to recognize this state because only the inner needle guard "blue" color would be visible: thus, the medicated module in the "blue" state would indicate to the user that the medicated module 100 has already been used for a first injection and that any subsequent dose would comprise only the primary medicament 105 contained in the cartridge 103 and not the secondary medicament 120 contained in the reservoir 118. The blue state would also confirm to the user that the outer needle guard 134 remains in the locked out state.

Where the drug delivery device 102 comprises a dose setter 140, a dose of the drug delivery device 102 may be set using the dose setter 140 (see FIG. 7) in a normal manner known in the art (e.g., by dialing out the appropriate number of units). The single dose setter 140 may be operably connected to the cartridge 103 containing primary medicament 105. Dispense of the medicaments 105, 120 may then be achieved by subcutaneously injecting the medicaments via activation of a dose button 142 on device 102. The dose button 142 may be any triggering mechanism that causes the dose of the first medicament that was set by the dose setter to move distally towards the distal end of the device.

As will be described in greater detail below, a user may use the dose setter 140 in order to prime the device or inject a first and/or second dose of medicament. Specifically, a user may use the dose setter 140 to (i) prime the device, (ii) deliver a first injection, (iii) prime the device as needed after the first injection, and (iv) deliver a second injection.

After a user attaches the medicated module 100 to the delivery device 102 and before a user injects a dose of medication, a user may prime the device. The act of priming the device is described with reference to FIG. 2. The user may use the dose setter 140 (see FIG. 7) in order to prime the device. For example, a user may repeatedly select and dispense (to air) a small dose of 1-3 units until liquid is seen exiting the outlet needle in order to prime the device.

As described above, prior to a first injection, the second medicament 120 is contained within the sealed reservoir 118 that is not in fluid communication with either the first needle 114 that connects with the primary device or the second needle 116 which is the output needle. However, the first and second needles 114, 116 are in fluid communication with one another due to a bypass path that is directed around reservoir 118. During priming, when a user presses the dosing button 142, the medicament 105 may be forced in the distal direction from cartridge 103 toward needle 116. Therefore, during priming, the first medicament 105 may be dispensed from the cartridge 103, through the first needle 114, around the sealed reservoir 118 and to the output needle 116. This bypass path is depicted in FIG. 2 by a plurality of arrows 160.

This bypass path 160 around the sealed reservoir 118 is preferably created by channels 162 around each side of the reservoir. These channels 162 allow for fluid communication between the first needle 114 and the second needle 116. Medicated module 100 also may include a bypass cavity 190 that is located below the bottom seal 132 of reservoir 180. The bypass cavity 190 is in fluid communication with the first and second needles 114, 116. As illustrated in FIG. 2, importantly, the bypass cavity 190 has a width that is greater than the width of the shuttle 112.

After a user primes the device 102, a user may then select a dose for a first injection using the dose setter 140. As mentioned above, a user may inject a first dose that includes the fixed predetermined dose of the second medicament 120 and a potentially variable dose of a first medicament 105. A user may dial a desired dose of the first medicament using the dose setter 140.

When a user injects the first dose, the user may press the device 102 against an injection site, such as the user's leg or stomach. When a user presses the device 102 against an injection site, the needle guard assembly 122 moves in a proximal direction 180 to a first retracted position. This first retracted position is illustrated in FIG. 3.

During insertion, both needle guards 134, 136 of the needle guard assembly 122 are displaced in the proximal direction towards the drug delivery device 102. Towards the end of the needle guard assembly's 122 displacement, the inner needle guard 136 contacts shuttle 112 at, for example, contact points 320 and 322. The shuttle 112 is displaced upwards (i.e. in the proximal direction) along with this proximal displacement of the needle guard assembly 122. In particular, the shuttle 112 is displaced in the direction of the device cartridge 103.

As the shuttle 112 is displaced proximally, the first and second wavy springs 130, 132 compress. In addition, as the proximal end of the shuttle 112 moves past the bypass cavity 190, any excess fluid remaining in the bypass path 160 or channels 162 a, b would be displaced into the toroidal cutout 111 of the shuttle 112. In addition, the shuttle 112 maintains its fluidic seal with the housing by way of the first and second shuttle sealing rings 140, 144 that move along this housing inner wall. As such, the configuration of the shuttle and the width of the bypass cavity 190 allow the bypass cavity 190 to be in fluid communication with any residual priming volume of the first medicament 105 remaining in the bypass paths 160 and bypass cavity 190 to as to prevent any potential hydraulic lock that might occur.

The displacement of the shuttle 112 and the consequent compression of both the first and second springs 130, 132 causes (i) the second needle 116 to pierce the bottom seal 126 of the reservoir 118 and (ii) the first needle 114 to pierce the top seal 124 of the reservoir 118. As can be seen in comparing FIG. 3 with FIG. 1, after an initial injection, the wavy springs 130, 132 will compress. Due to this compression and the fact that the first needle 114 is fixed in the housing 104 and the second needle 116 is fixed in the shuttle 112, the first and second needles 114, 116 pierce the top and bottom seals 124, 126 respectively. Piercing of top and bottom seals 124, 126 now opens fluid communication between the first and second medicaments 105, 120. This open fluid communication allows these two medicaments to be dispensed through operation of the dispense mechanism of the drug delivery device 102.

As such, when a user depresses the dosing button 142 of dose setter 140, medicament 105 from cartridge 103 is forced through first needle 114 toward the reservoir, and in turn toward output needle 116. This flow in turn forces second medicament 120 from reservoir 118 to flow through output needle 116. Therefore, a first dose of the fixed predetermined dose of the second medicament 120 and a potentially variable dose of a first medicament 105 is administered to the user through output needle 116.

At the end of the vertical displacement of the needle guard assembly 122, clip features 302, 304 in the medicated module 100 engage with corresponding clip features 306, 308 disposed on the inside of the outer needle guard 134, respectively. Further, the shuttle 112 remains in its displaced position due to clip features 310, 312, which respectively engage with corresponding clip features 314, 316. It should be understood that the clip features are provided as one example. Other engagement features or locks are possible as well.

Figure 4A:
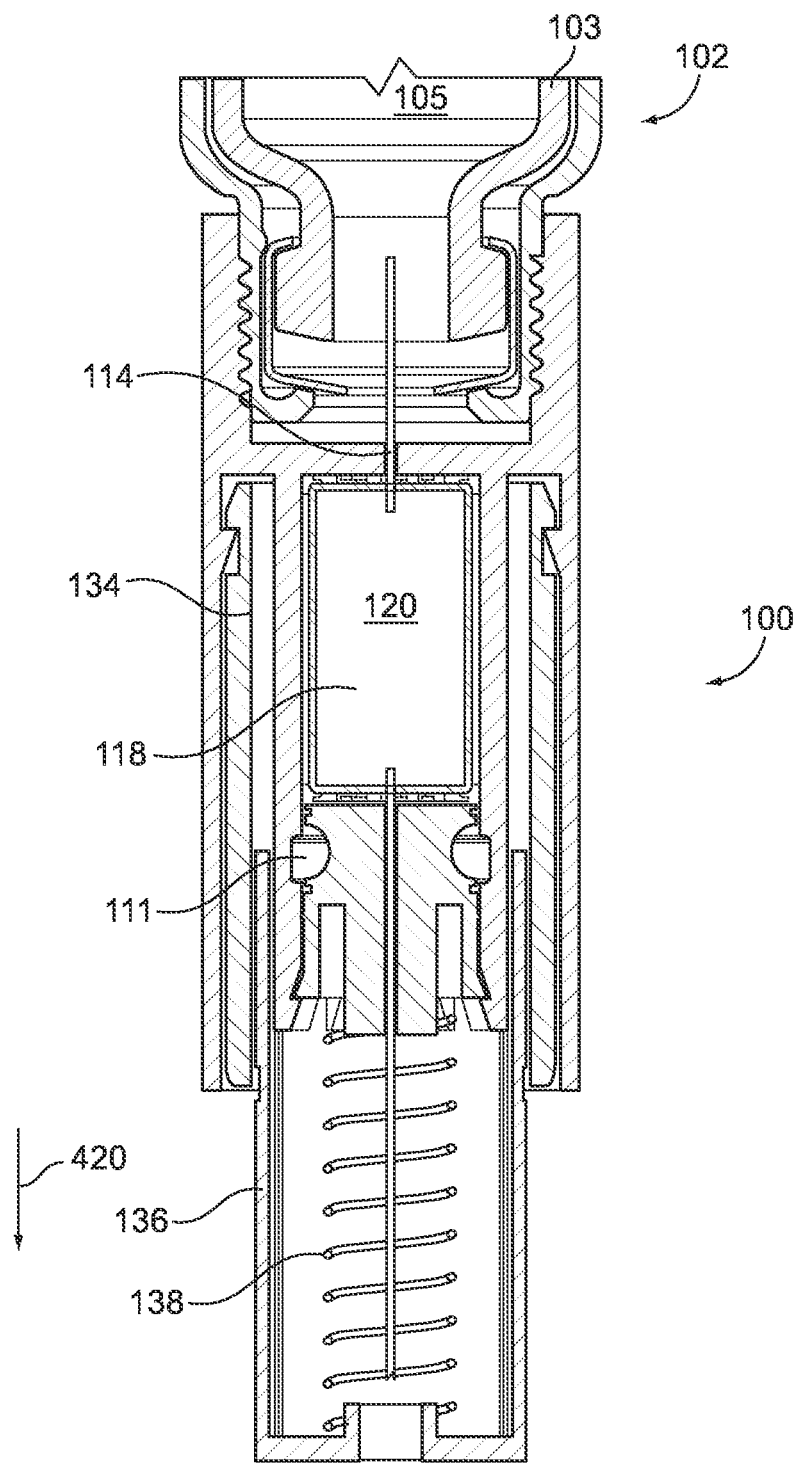
FIG. 4A illustrates a sectional view of the medicated module of FIG. 1 with the inner guard in a first extended position.
Figure 4B:
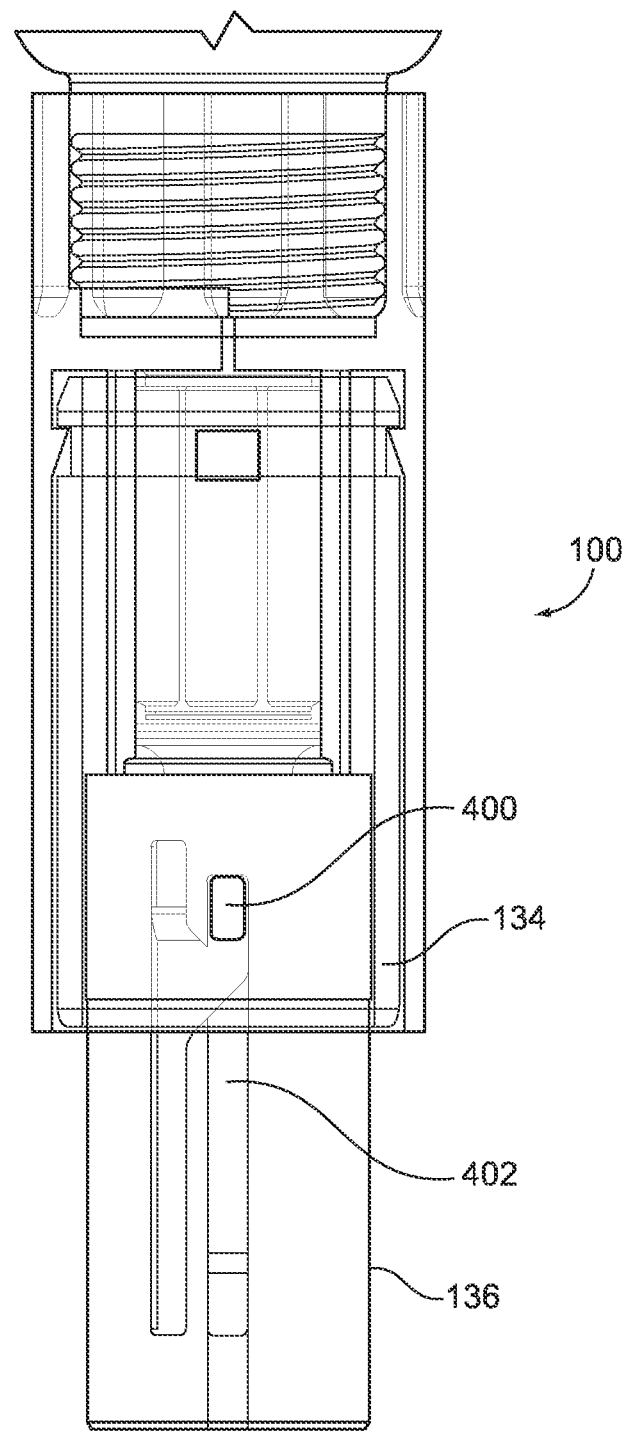
FIG. 4B illustrates a side elevation view of the medicated module shown in FIG. 4A.

After an initial injection and after the drug delivery device 102 and the medicated module 100 are removed from the injection site, the outer needle guard 134 remains in the fully retracted position due to the engagement of the needle-guard clip features 302, 304, 306, 308. In addition, the shuttle 112 remains in its displaced position due to the engagement of the shuttle clip features 310, 312, 314, 316. However, the inner needle guard 136 returns axially in the distal direction 420 to a first extended position. The axial return to this first extended position is depicted in FIGS. 4A and 4B. The inner needle guard 136 under the force of the biasing mechanism 138 is forced in the distal direction 420. In a preferred embodiment, the biasing mechanism is a spring. Other biasing mechanisms are possible as well.

As the inner needle guard 136 descends to the first fully extended position, a pip feature 400 in the outer needle guard 134 runs in a groove 402 present in the inner needle guard 136. The inner needle guard 136 is constrained rotationally, so that it is the outer, retained, needle guard 134 that is forced to rotate as the pip 400 follows the groove. One advantage of constraining the rotation of the inner needle guard 136 is that this inner guard is prevented from rotating during injection (i.e., it would not rotate while being placed against the patient's skin). Finally, at a predetermined position, the pip 400 springs radially into an inner groove 404.

After the inner needle guard 136 returns to the first fully extended position, a user may, in certain situations, desire to inject another dose of the first medicament 105 contained in the drug delivery device. As mentioned above, a user may desire a second dose for a number of reasons. As just one example, a user may need to top up their initial dose (i.e., a combination dose of both the first and second medicament) with an additional dose of the first medicament. In an alternative arrangement, the medicated module 100 could be provided with a temporary lockout. For example, an optional path may be provided for the pip 400 in the groove 402 where the user rotates the inner guard 136 to enable a temporary lock out feature. Alternatively, the second guard 136 may be provided with a small detent feature (or other similar mechanical feature) that provides a certain level of temporary 'lock-out' after injection of the first dose. With such a proposed temporary 'lock-out' feature, a user could easily overcome such lock out by a deliberate action to retract the needle guard 136. Other examples are possible as well.

Before injecting the second dose with the inner needle guard 136 in the lower extended position as illustrated in FIGS. 4A and 4B, a user may prime the device 102 yet again. As mentioned above, a user may prime the device 102 using dose setter 140. During this priming step, the first medicament may flow from cartridge 103 to needle 114, through reservoir 118 to output needle 116, and then out via the output needle 116. This priming is performed only with the first medicament 105 since the second medicament 120 will have already been dispensed during the initial first injection. Again, where the inner and outer needle guards have a unique color coding scheme, this would be indicated to the user since only the colored inner needle guard would be visible to the user.

After priming the device for a second time, the user may inject a second dose of the primary medicament 105 using the dose setter 140. This second injection would be via a non-sterile needle. In one preferred embodiment, it is envisaged that a user would administer this second dose nearly immediately after administering the first dose. As mentioned above, a user may inject a second dose that includes a potentially variable dose of a first medicament 105. For example, a user may inject 20 units of the first medicament 105. As another example, a user may inject 40 units of the first medicament 105. Other examples of variable doses of the first medicament are possible as well.

Figure 5A:
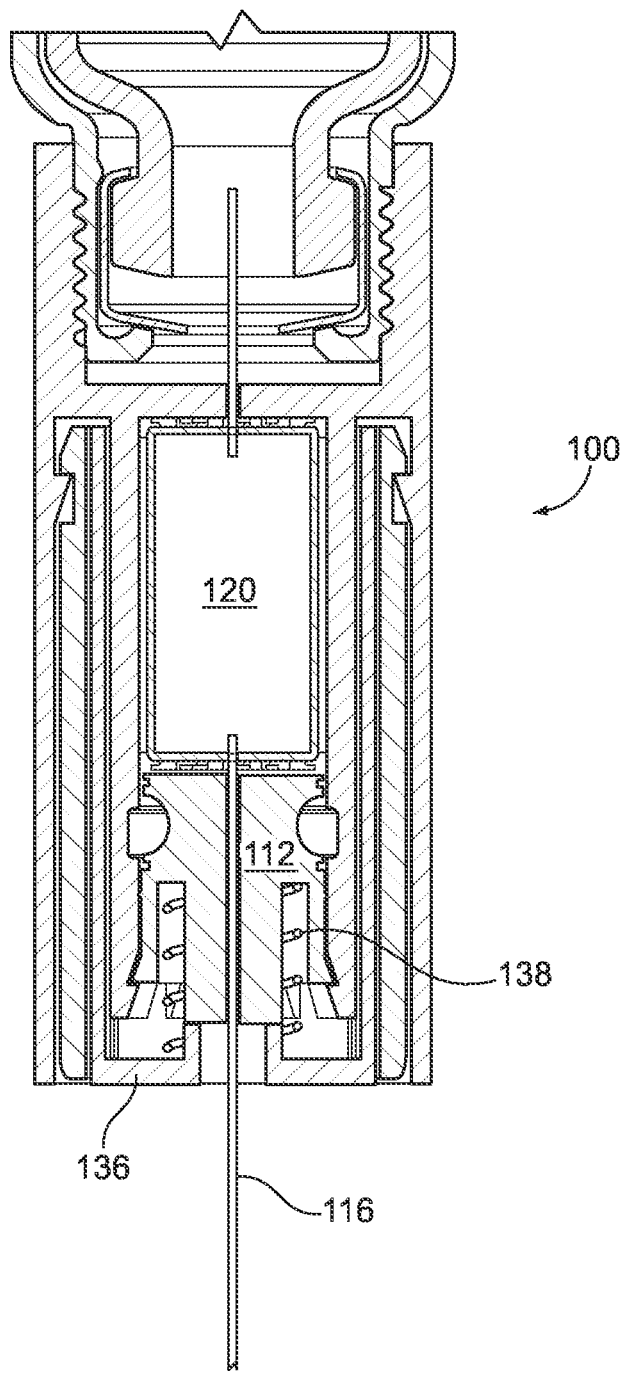
FIG. 5A illustrates a sectional view of the medicated module of FIG. 1 in a second retracted position.
Figure 5B:
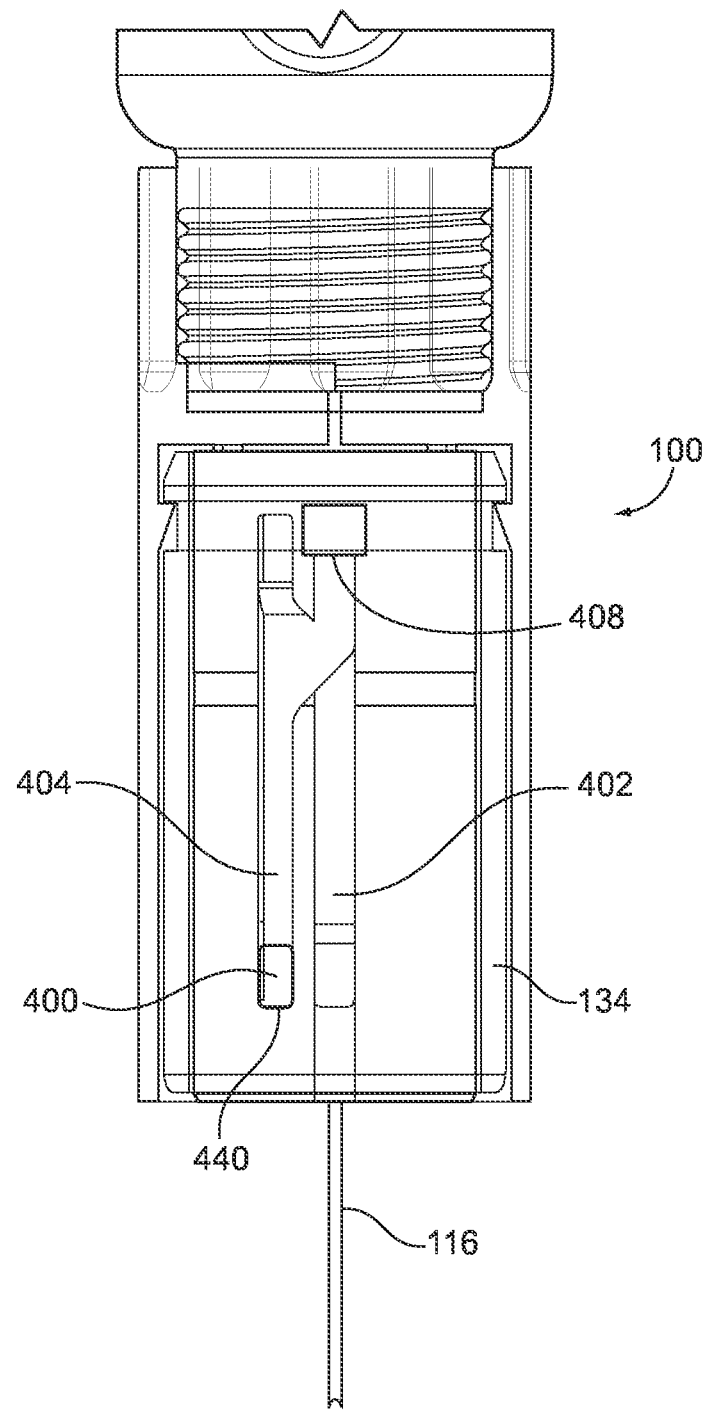
FIG. 5B illustrates a perspective view of the medicated module shown in FIG. 5A.

When a user injects the second dose, the user may press the device against an injection site, such as the user's leg or stomach. When a user presses the device 102 against an injection site, the inner needle guard 136 moves in proximal direction 180 to a second retracted position. This second retracted position is illustrated in FIGS. 5A and 5B. During movement to this second fully retracted position, as can be seen in FIG. 5B, the pip 400 follows the path of the inner groove 404 as the inner needle guard 136 moves into the second retracted position. Specifically, pip 400 moves from first proximal end 408 of inner groove 404 to distal end 440 of inner groove 404.

Figure 6A:
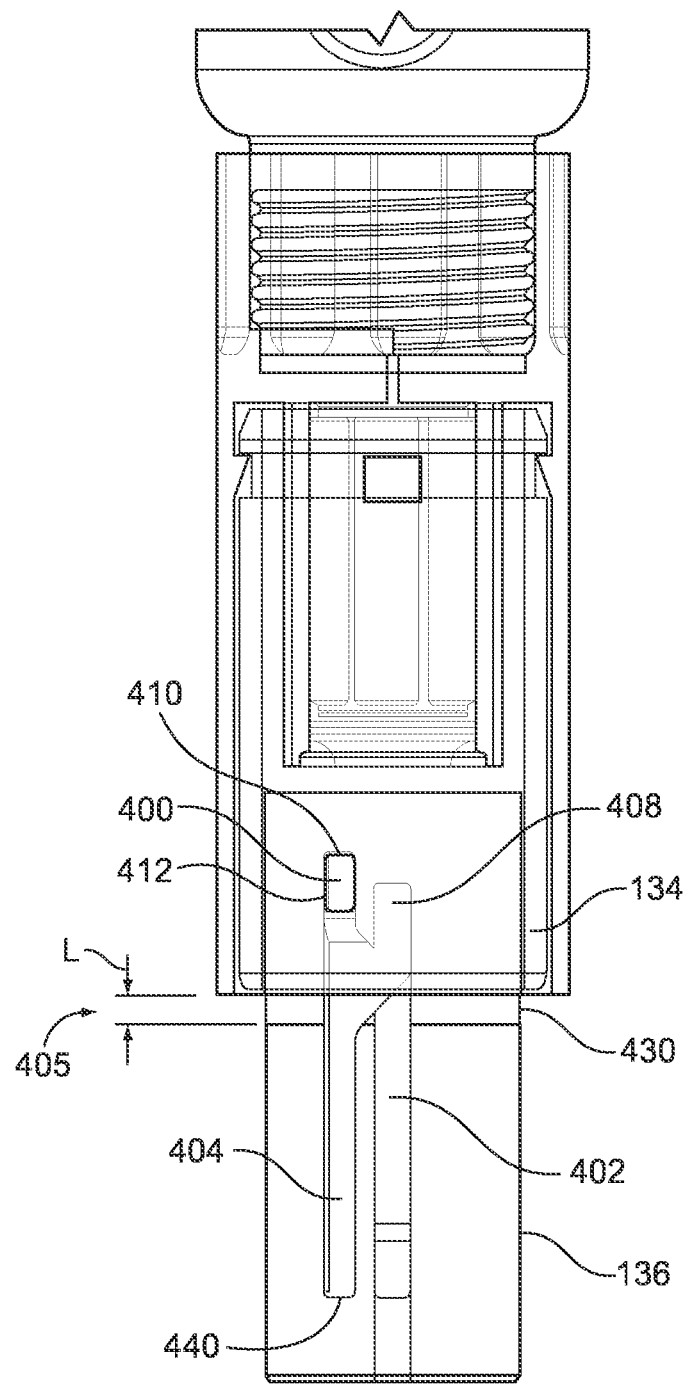
FIG. 6A illustrates a perspective view of the medicated module of FIG. 1 with the inner guard in a second, locked-out extended position.
Figure 6B:
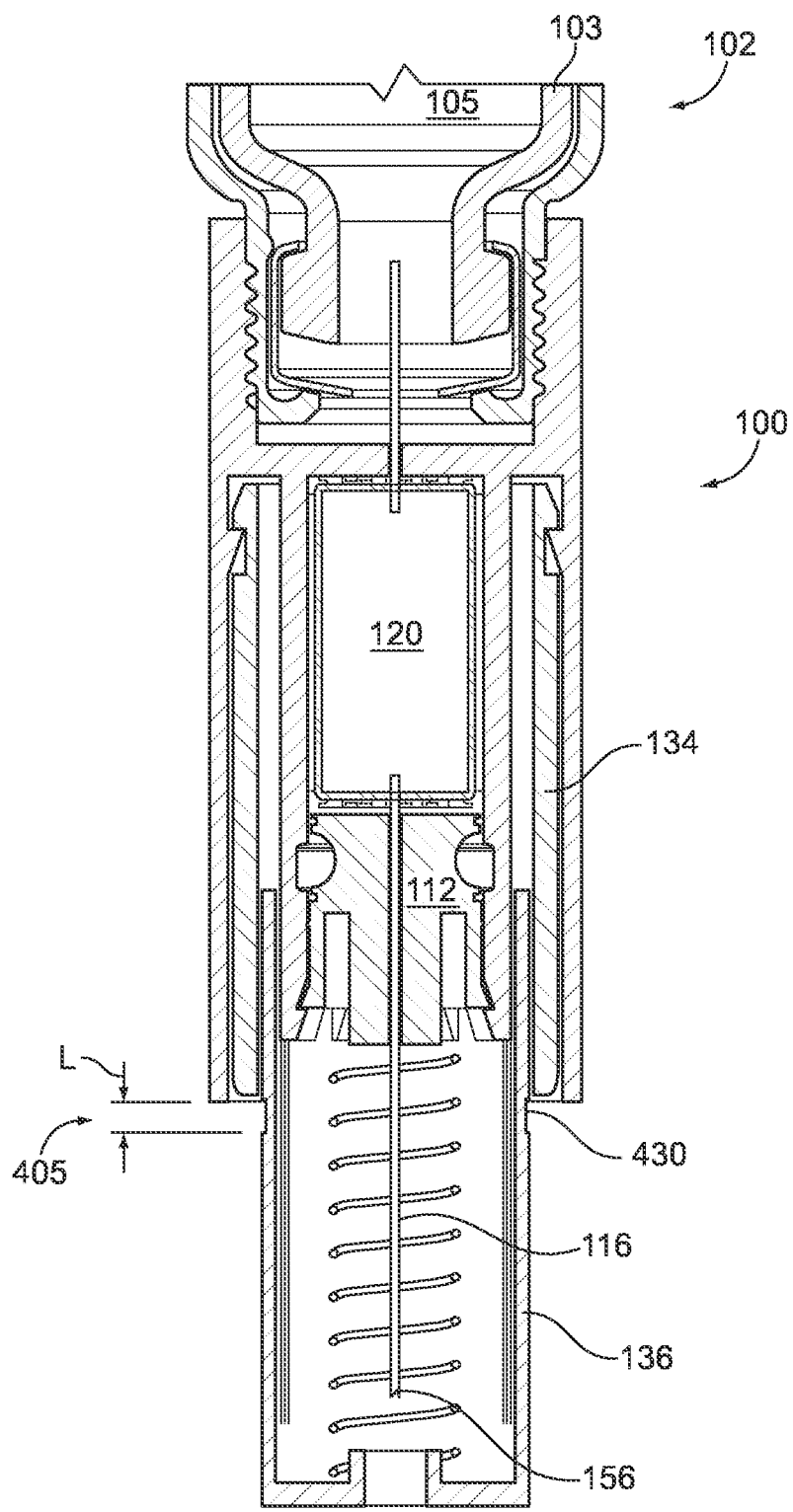
FIG. 6B illustrates a sectional view of the medicated module shown in FIG. 6A.

After the second injection, when the drug delivery device 102 and the medicated module 100 are removed from the injection site, the inner needle guard 136 extends to a second extended position under the force of biasing spring 138. FIG. 6A illustrates a perspective view of the medicated module of FIG. 1 with the inner guard 136 in this second, locked-out extended position. FIG. 6B illustrates a sectional view of the medicated module shown in FIG. 6a. As illustrated, in a preferred arrangement, the device 102 locks out after the second injection. As can be seen in FIG. 6A, the pip 400 follows the path of the inner groove 404. The inner groove at the second proximal end 410 has a recess 412. The pip 400 locks into the recess 412 in the inner needle guard 136. Therefore, the inner needle is locked in. As a result, the medicated module 100 can no longer be used.

Importantly, in one preferred arrangement, the inner needle guard 136 extends to a second extended position that is greater in length than the first extend position after the first dose. For example, as illustrated in FIGS. 6A and 6B, when compared to the distance the inner guard has moved in FIGS. 4A and 4B, this guard 136 moves an additional length of L 405 in the distal direction. The additional length L 405 that the inner guard 136 moves after the second injection is a mechanical function of the end stop of the second groove 410 and therefore can either be lengthened or shortened as desired. One advantage of such a configuration, is that the inner guard 136 may have an indicia 430 visible to a user indicating that the inner guard 136 is locked to the outer guard 134. In an example embodiment, a visual indication 430 of the lock-out may be disposed on the outside of the inner needle guard 136. For example, in an example embodiment, a red line may be located on the outside of the inner needle guard 136 to indicate that the second needle 116 can no longer be used.

In an alternative arrangement, the outer needle guard 134 could comprise a substantially opaque material and therefore conceal indicia until after the first injection has been completed and the inner guard 136 moves back to its first extended position. In yet another alternative arrangement, the outer guard 134 could comprise a transparent material while containing a color pigment that corresponds with the second medicament 120. In such an arrangement, the internal guard 136 could comprise a different color (possibly also transparent) that corresponds with the primary medicament 105 so as to provide a visual indication as to what will be dispensed (i.e., medicament wise) during the first and second use is provided to a user. The inner and outer needle guards 134, 136 could be either fully colored, or done as colored banding depending on which provides the clearest indication to the patient as to what they will receive.

Locking the needle guard assembly 122 in the distal position in this manner provides a number of beneficial features. First, it prevents a user from re-using a non-sterile medicated module 100 after the second dose. Second, the locked needle guard 122 protects and substantially conceals the needle 116 and therefore reduces the risk of a potential inadvertent needle stick. In addition, by substantially concealing the needle 116, the locked needle guard assembly 122 acts to reduce any potential needle fear, needle phobia or needle anxiety that a patient may experience.

After the medicated module 100 is locked out, a user may disconnect the medicated module 100 from the drug delivery device 102. The medicated module 100 may then be disposed of. Alternatively, the user could dispose of the medicated module 100 along with the drug delivery device 102. This may occur, for example, when a user tops up the remaining dose of the first medicament 105 left in the drug delivery device 102.

The operation of the module 100 does not need to be performed in connection with the delivery of a dose to a user. No interaction of the medicated module with the human or animal body needs to take place. In particular, the steps of setting and dispensing a dose of the first medicament 105 and the second medicament held in the reservoir 118 of the module 100 may be performed for testing the functionality of the module 100, for example.

A typical drug delivery device 102 in accordance with embodiments contains a cartridge or other reservoir of medication. This cartridge is typically cylindrical in shape and is usually manufactured in glass. The cartridge is sealed at one end with a rubber bung and at the other end by a rubber septum. The injection device may further comprise a dose setter; the dose setter may be operably connected to the reservoir. The injection device comprises a dose button; the dose button may be operably connected to the reservoir. The dose button may be any triggering mechanism that causes the dose of the medicament that was set by the dose setter to move distally towards the distal end of the device. In a preferred embodiment, the dose button is operably connected to a spindle that engages a piston in the reservoir. In a further embodiment the spindle is a rotatable piston rod comprising two distinct threads. The drug delivery device is designed to deliver multiple injections. The delivery mechanism is typically powered by a manual action of the user as described above; however, the injection mechanism may also be powered by other means such as a spring, compressed gas or electrical energy.

In certain embodiments where the medicated module contains a single dose of a medicament, the module is attached to a drug delivery device in order to administer the single dose in the reservoir to a patient. In other words, the medicated module cannot be used as a stand-alone injection device. This is because the module does not have a dose delivery mechanism and instead relies on the dose delivery mechanism contained in the drug delivery device to which it is attached.

Exemplary embodiments of the present invention have been described. Those skilled in the art will understand, however, that changes and modifications may be made to these embodiments without departing from the true scope and spirit of the present invention, which is defined by the claims.

REFERENCE NUMERALS

100 medicated module
102 drug delivery device
103 device cartridge
104 housing of medicated module
105 primary first medicament
106 proximal end of module
107 septum/membrane of device cartridge
108 distal end of module
110 connector
111 toroidal cutout
112 shuttle
114 first needle
115 proximal end of shuttle
116 second needle
118 reservoir of medicated module
120 second medicament
122 needle guard assembly
124 first pierceable membrane/top seal
126 second pierceable membrane/bottom seal
130 proximal wavy spring (first biasing member)
132 distal wavy spring (second biasing member)
134 first guard/outer guard
136 second guard/inner guard
138 biasing member of guard assembly
140 dose setter
140 first sealing ring
142 dose button
144 second sealing ring
150 first piercing end of first needle
152 second piercing end of first needle
154 first piercing end of second needle
156 second piercing end of second needle
160 arrows indicating bypass path
162 channels of bypass path
180 proximal direction
190 bypass cavity
302, 304 clip feature in medicated module
306, 308 clip feature at outer needle guard
310, 312 clip feature at shuttle
314, 316 clip feature at housing
320, 322 contact point of shuttle and inner needle guard
322 contact point of shuttle and inner needle guard
400 pip feature in outer needle guard
402 groove in inner needle guard
404 inner groove
405 additional length L
408 first proximal end of inner groove
410 second proximal end of inner groove
412 recess at inner groove
420 distal direction
430 indicia
440 distal end of inner grove

We claim:
1. A medicated module attachable to a drug delivery device,
wherein the drug delivery device comprises a primary reservoir of a first medicament and wherein the medicated module comprises a second medicament, the medicated module comprising:
a reservoir comprising the second medicament,
a housing having a proximal end and a distal end, where the housing is being configured for attachment to the drug delivery device; wherein the reservoir of the medicated module is positioned within the housing by a first biasing member and a second biasing member;
a first needle fixed in the housing,
a second needle fixed in a shuttle, wherein the shuttle is configured for axial movement relative to the housing, first needle guard and a second needle guard adapted and arranged to provide protection against the second needle and operable connected to move together axially in a proximal direction with respect to the housing during a first movement for a first application to an injection site, wherein the first needle guard is configured to mechanically cooperate with the shuttle for moving the shuttle with respect to the housing, wherein a movement of the shuttle in the proximal direction opens fluid communication between the reservoir of the medicated module and at least one of the first and the second needle.

2. The medicated module of claim 1, wherein the shuttle is configured for axial movement so as to cause the first and second biasing members to compress and thereby allow fluid communication between the medicament in the reservoir of the medicated module and the first and second needle.

3. The medicated module of claim 1, being configured to lock the shuttle from axial movement when the first needle guard is moved axially towards the proximal end of the housing.

4. The medicated module of claim 1, wherein the housing is configured to lock the first needle guard during axial movement of the first needle guard in the proximal direction such that a relative axial movement of the housing and the first needle guard is disabled.

5. The medicated module of claim 1 configured such that the second needle guard is movable in a distal direction after axial movement in the proximal direction during a first application to an injection site.

6. The medicated module of claim 1 configured such that the second needle guard is locked to the first needle guard after a second application to an injection site such that a relative axial movement of the second needle guard and the first needle guard is disabled.

7. The medicated module of claim 1, comprising indicia visible to a user indicating the locking state of at least one of the first and second needle guard.

8. The medicated module of claim 1 further comprising a bypass path bypassing the reservoir of the medicated module and being configured to be in fluid communication with the first and second needles before a first application to an injection site.

9. The medicated module of claim 1 being configured such that the needle guard locks out the second needle after the second needle has been used to inject more than one dose of the medicament contained in the primary reservoir such that the second needle is disabled from being used for a further injection.

10. A drug delivery system to deliver two or more medicaments comprising a medicated module according to claim 1 and further comprising: a primary reservoir of medicament containing at least one drug agent; where the medicated module is configured for fluid communication with the primary reservoir.

11. A method for testing a medicated module, the method comprising the steps of:
A) Providing the medicated module according to claim 1;
B) Attaching the medicated module to a drug delivery device, the device comprising a primary reservoir of medicament containing at least one drug agent;
C) Setting a dose of the medicament using a single dose setter of the drug delivery device;
D) Performing a priming step by means of activating a dose button on the drug delivery device such that medicament of the primary reservoir is expelled through the second needle;
E) Moving the first and second needle guards proximally such that the shuttle is moved proximally and such that fluid communication is established between the needles and the reservoir;
F) Setting a variable dose of the medicament of the primary reservoir;
G) Activating the dose button on the drug delivery device to cause the set dose of the first medicament from the primary reservoir to flow in a distal direction;
H) Forcing the set dose of the first medicament and the single dose of the second medicament through the second needle.

12. The method of claim 11, further comprising the step of
I) Locking the first needle guard in a retracted position after the first needle guard was moved proximally and after fluid communication was established.

13. The method of claim 11, further comprising the steps of
J) Moving the second needle guard proximally;
K) Setting a further variable dose of the medicament of the primary reservoir;
L) Activating the dose button on the drug delivery device to cause the further dose of the first medicament from the primary reservoir to flow in the distal direction;
M) Forcing the further dose of the first medicament through the second needle;
N) Locking the second needle guard in an extended position after the further dose of the medicament was expelled.

* * * * *